(12) United States Patent
Sugizaki

(10) Patent No.: US 11,391,695 B2
(45) Date of Patent: Jul. 19, 2022

(54) METHOD FOR DETERMINING MOLECULAR PROBE

(71) Applicant: KABUSHIKI KAISHA TOSHIBA, Minato-ku (JP)

(72) Inventor: Yoshiaki Sugizaki, Fujisawa (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 341 days.

(21) Appl. No.: 16/299,448

(22) Filed: Mar. 12, 2019

(65) Prior Publication Data

US 2020/0088682 A1 Mar. 19, 2020

(30) Foreign Application Priority Data

Sep. 19, 2018 (JP) .............................. JP2018-174395

(51) Int. Cl.
*G01N 27/447* (2006.01)
*C12Q 1/6876* (2018.01)

(52) U.S. Cl.
CPC ..... *G01N 27/44778* (2013.01); *C12Q 1/6876* (2013.01); *G01N 27/44795* (2013.01)

(58) Field of Classification Search
CPC ....... G01N 27/44756; G01N 27/44773; G01N 27/44778; G01N 27/44782; G01N 27/44795; C12Q 1/6811; C12Q 1/6876
See application file for complete search history.

(56) References Cited

FOREIGN PATENT DOCUMENTS

| JP | 2003-315329 A | 11/2003 |
|----|---------------|---------|
| JP | 2006-511807 A | 4/2006 |
| JP | 2008-3028 A | 1/2008 |
| JP | 2014-145680 A | 8/2014 |

OTHER PUBLICATIONS

N. Savory, et al., Two-dimensional electrophoresis-based selection of aptamers against unidentified protein in a tissue sample, Analytical Letts, vol. 46, pp. 2954-2963 (2013) (Year: 2013).*
Y. Liu, et al. DNase-Mediated Single-Cycle Selection of Aptamers for Proteins Blotted on a Membrane, Anal. Chem., vol. 84, No. 18, pp. 7603-7606 (2012) (Year: 2012).*
Z. Novakova, et al., Separation of nuclear protein complexes by blue native polyacrylamide gel electrophoresis, Electrophoresis, vol. 27, pp. 1277-1287 (2006) (Year: 2006).*

\* cited by examiner

*Primary Examiner* — Maris R Kessel
(74) *Attorney, Agent, or Firm* — Oblon, McClelland, Maier & Neustadt, L.L.P.

(57) ABSTRACT

According to one embodiment, a method for determining a molecular probe is a method for determining a molecular probe that captures a target compound. The method comprises (S1) making candidate molecules of one kind in contact with a target compound, and electrophoresing an obtained mixture on a gel, and (S2) determining the candidate molecule as the molecular probe that captures the target compound in following case when the band of the candidate molecule is separated into a plurality of bands, or when the candidate molecule forms a broad band in the electrophoresed direction on the gel after the electrophoresing.

22 Claims, 9 Drawing Sheets

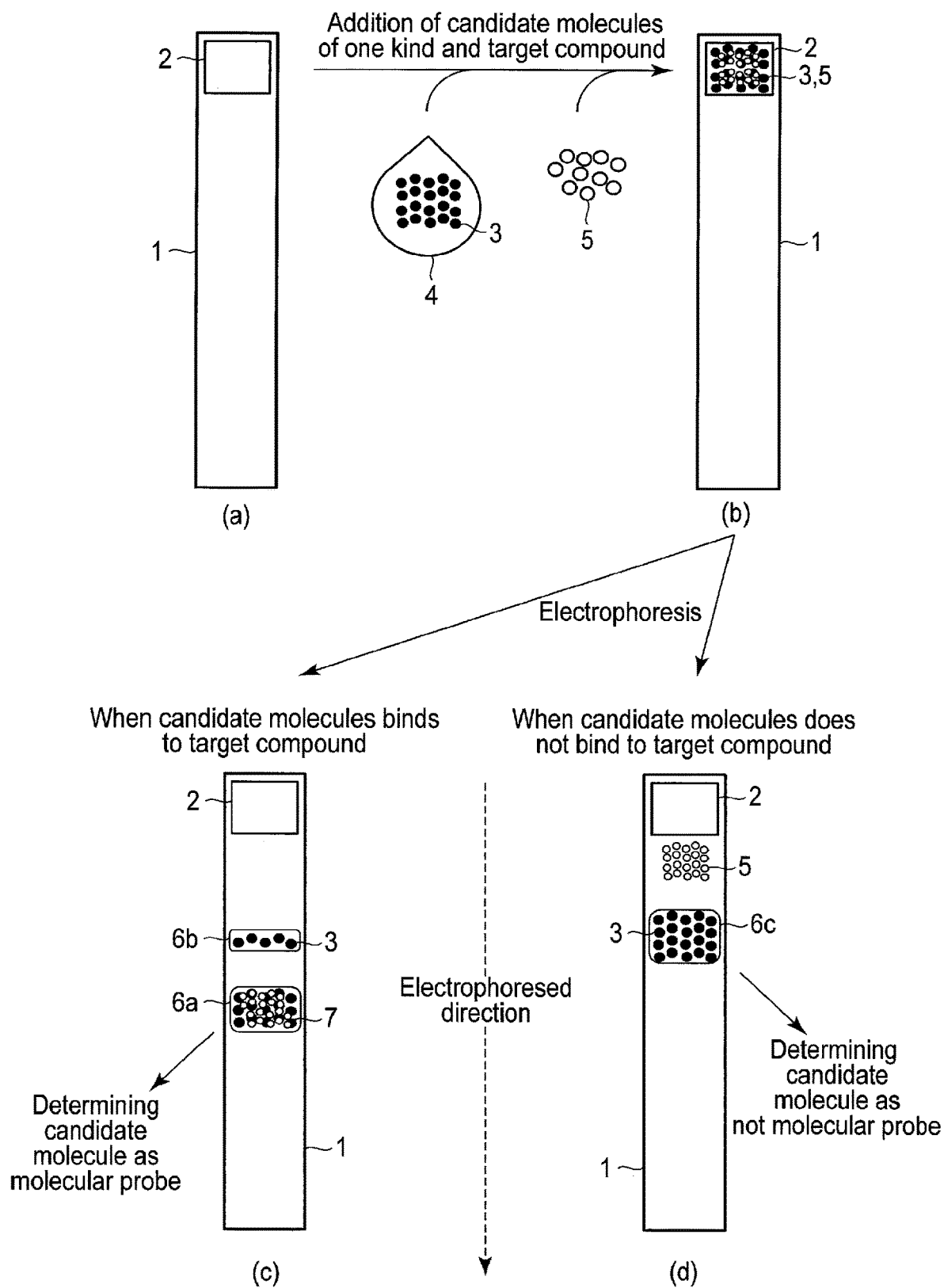
F I G. 2

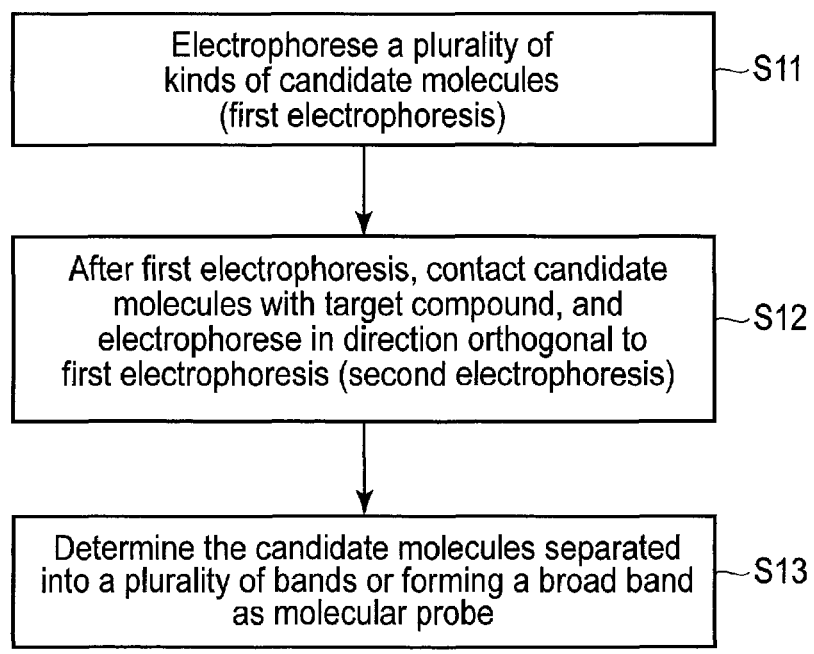
F I G. 3

(a)

(b)

US 11,391,695 B2

METHOD FOR DETERMINING MOLECULAR PROBE

CROSS-REFERENCE TO RELATED APPLICATIONS

This application is based upon and claims the benefit of priority from Japanese Patent Application No. 2018-174395, filed Sep. 19, 2018, the entire contents of which are incorporated herein by reference.

FIELD

Embodiments described herein relate generally to a method for determining a molecular probe.

BACKGROUND

In the field of compound detection, molecular probes are often used, which capture a target compound to be detected selectively or specifically. For example, a target compound can be labeled or separated by a molecular probe, which is useful for efficient detection and separation and the like of the target compound.

Accordingly, researchers have been seeking optimal molecular probes for target compounds. Molecular probes for certain target compound can be found, for example, by investigating whether various candidate molecules bind to the target compound or not. As such a method, for example, electrophoresis or column chromatography is often used.

In the method using electrophoresis, after making a target compound into contact with various candidate molecules, electrophoresis is performed. Then, the candidate molecule bound to the target compound is determined as a molecular probe that captures the target compound by difference of the electrophoretic distance of the candidate molecule not bound to the target compound.

In the method using column chromatography, for example, a target compound is immobilized on a solid phase of a column and candidate molecules in a liquid phase is flowed through the column. Then, the candidate molecule that binds with the target compound and remains on the solid phase is determined as the molecular probe for the target compound.

On the other hand, detection of low molecular weight compounds is greatly useful in various fields such as narcotic investigation, doping examination, medical diagnosis and the like. However, since a low molecular weight compound has a small molecular weight and a simple structure, it is very difficult to detect it separately from other compounds having a similar structure. Accordingly, development of a method for detecting a low molecular weight compound with high sensitivity is required.

BRIEF DESCRIPTION OF THE DRAWINGS

FIG. 2 shows schematic diagrams of the steps of a method for determining a molecular probe of one embodiment.

FIG. 3 shows a flowchart of a method for determining a molecular probe of one embodiment.

DETAILED DESCRIPTION

In general, according to one embodiment, a method for determining a molecular probe is a method for determining a molecular probe that captures a target compound. The method comprises:

(S1) making candidate molecules of one kind in contact with a target compound, and electrophoresing an obtained mixture on a gel; and (S2) determining the candidate molecules as the molecular probe that captures the target compound in the following case:

when the band of the candidate molecules is separated into a plurality of bands, or when the candidate molecules form a broad band in the electrophoresed direction on the gel after the electrophoresing.

According to the second and third embodiments, a method for determining a molecular probe from a plurality of candidate molecules is provided.

Hereinafter, various embodiments are described with reference to the drawings. Each of the drawings is a schematic diagram that shows each embodiment and that promotes understanding of the embodiment, and its shape, dimension, ratio, and the like are sometimes different from actual ones. However, these drawings can be appropriately modified in consideration of the following description and known techniques.

Hereinafter, a method for determining a molecular probe according to the first to third embodiments is described.

First Embodiment

Figure 1:
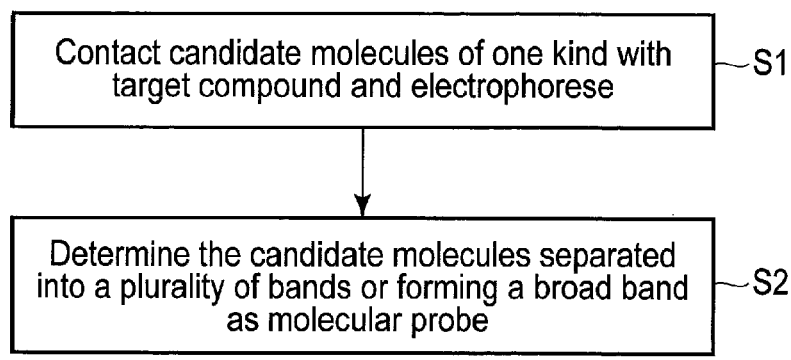
FIG. 1 shows a flowchart of a method for determining a molecular probe according to an embodiment.

FIG. 1 is an outline flow showing a method for determining a molecular probe according to first embodiment. The method comprises:

(S1) making candidate molecules of one kind in contact with a target compound, and electrophoresing an obtained mixture on a gel; and (S2) determining the candidate molecules as the molecular probe that captures the target compound in the following case:

when the band of the candidate molecules is separated into a plurality of bands, or when the candidate molecules form a broad band in the electrophoresed direction on the gel after the electrophoresing.

Hereinafter, the principle that a molecular probe capturing a target compound can be determined by performing each of the above steps is described with reference to FIG. 2. FIG. 2 is schematic diagram showing the steps of a method for determining a molecular probe.

First, a solution 4 containing candidate molecules of one kind (candidate molecules 3) and a target compound 5 are added to a recess 2 formed at one end of a first gel 1 as shown in (a) of FIG. 2. As a result, the candidate molecules 3 is made in contact with the target compound 5 ((b) of FIG. 2). The candidate molecules 3 can be pre-labeled so that it can be optically observed on the gel.

Next, the first gel 1 is subjected to electrophoresis. The electrophoresed direction is a direction from the end to which the solution 4 is added to the other end of the first gel 1.

As shown in (c) of FIG. 2, when the candidate molecules 3 is a molecule capable of binding to the target compound 5, the candidate molecules 3 is separated into two bands 6a and 6b on the first gel 1. Alternatively, the band becomes broad in the electrophoresed direction. The reason why the bands are separated into two or the band becomes broad is described below.

The candidate molecules 3 to be used are of one kind, and multiple molecules of this kind of the candidate molecules 3 are contained in the solution 4. When the candidate molecules 3 is a molecule having binding ability to the target compound 5, when it comes into contact with the target compound 5, some molecules bind to the target compound 5, but not all the candidate molecules 3 bind to the target compound 5. In other words, there are ones that bind to the target compound 5 to form a complex 7 and others that do not bind to the target compound 5. In addition, transition between a bound state and an unbound state may occur since the bond between the candidate molecules 3 and the target compound 5 is usually an equilibrium reaction which reversibly changes due to factors such as the structures of the candidate molecules 3 and the target compound 5, the dissociation constant and free energy change. In this way, it may occur with a very high probability that some of the molecules of the candidate molecules 3 having the binding ability to the target compound 5 exist in an unbound state.

The complex 7 comprising the candidate molecules 3 and the target compound 5, and the candidate molecules 3 not bound to the target compound 5 are different in isoelectric point, molecular weight and/or higher order structure and the like, each other. Therefore, they are separated into the band 6a and the band 6b, respectively as shown (c) of FIG. 2. Alternatively, when the candidate molecules 3 having different time periods of binding to the target compound 5 are present in a mixed state, the separated bands are not clearly distinguished but take a form of a broad band. Here, the broad band is also called a separated band.

Accordingly, as shown in (c) of FIG. 2, the candidate molecules 3 separated into a plurality of bands or the candidate molecules 3 forming a broad band is regarded as a molecule that binds to the target compound 5 and can be determined as a molecular probe that captures the target compound 5.

On the contrary, as shown in (d) of FIG. 2, when the candidate molecules 3 is a molecule not bound to the target compound 5, the candidate molecules 3 is electrophoresed to form a band 6c and is not separated. In addition, the length of the band in the electrophoresed direction does not become broader beyond that assumed by free diffusion. In this case, it can be determined that the candidate molecule 3 is not a molecular probe that captures the target compound 5.

Further, it is also possible to judge whether there is a difference in band separation or broadening by comparing with the result of electrophoresis of the candidate molecules 3 without being made into contact with the target compound.

In the method described above, during electrophoresis, it is necessary for the candidate molecules 3 to be in a state capable of binding to the target compound 5 as a molecular probe. Accordingly, it is preferable to perform the electrophoresis, for example, by a method capable of maintaining the same 3-dimensional structure of the candidate molecules 3 as when being used as a molecular probe. As a result, it is possible to check whether the candidate molecules 3 having unmodified and original 3-dimensional structure binds to the target compound 5 or not, and it is possible to determine the molecular probe that captures the target compound 5 accurately.

Examples of such an electrophoresis method that can be used include isoelectric focusing (IEF), native electrophoresis and the like. The native electrophoresis can be, for example, BN (Bluenative) electrophoresis.

For example, IEF can be used when the target compound 5 is a compound having a charge. Native electrophoresis is preferably used when it is desired to determine a molecular probe whose 3-dimensional structure is changed by binding of the target compound 5. BN electrophoresis can be used when the candidate molecules 3 is a peptide or a protein and both the target compound 5 and the candidate molecules 3 have no charge or only a small charge.

When native electrophoresis or EN electrophoresis is used, when electrophoresis is kept running, bands continue to move and are migrated to the other end of the gel. Accordingly, electrophoresis must be stopped at a suitable time so that bands stop at observable positions. The time for electrophoresis varies depending on voltage, temperature, concentration, molecular weight and the like, but electrophoresis can be carried out, for example, for about 20 minutes to about 2 hours.

The first gel 1 may be any gel that is usually used in electrophoresis that can be used for the method of the embodiment. For example, the first gel 1 is a polyacrylamide gel, an agarose gel or the like. The type of the first gel 1 is selected according to the type of electrophoresis to be used. For example, when IEF is used, a gel having a pH gradient made from the above-described gel as a material can be used. Such a gel can be produced by a method of forming a pH gradient by adding a carrier ampholyte to a gel and applying an electric field, or a method of forming a pH gradient using acrylamide derivatives having side chains of various IPs at the same time as preparing the gel (IPG method) or the like.

The candidate molecule 3 is a molecule expected to be a molecular probe of the target compound 5. Examples of the candidate molecule 3 include protein, polypeptide, nucleic acid, aptamer and the like.

The labeling of the candidate molecules 3 may be carried out by, for example, a technique commonly used in electrophoresis that can be used in the method of the embodiment. For example, examples of the label that can be used include a fluorescent dye, a dyestuff, a radioisotope and the like. When the candidate molecule is protein or peptide, for example, Fluoresceinisothiocyanate isomer-I (FITC) can be used. FITC is a fluorescent molecule, and candidate molecules 3 can be labeled by making its isothiocyanate group react with a primary amine at the N-terminus of a protein or a peptide that is the candidate molecule. Alternatively, the candidate molecule 3 that is protein or peptide may be subjected to silver staining after electrophoresis. When BN electrophoresis is used, the candidate molecule 3 that is protein or peptide can be labeled by making the candidate molecules 3 be adsorbed by Coomassie Brilliant Blue. With the above-described label, band(s) can be observed, for example, by visual observation, transilluminator, or autoradiography.

The solution 4 is a solution in which the candidate molecules 3 are contained in an appropriate solvent. Examples of the solvent include distilled water, physiological saline, a buffer solution and the like. The solution 4 contains the candidate molecules 3 of one kind and has a composition not containing a substance that adversely affects determining of the molecular probe. Further, the solution 4 may have the same composition as the solvent when the candidate molecules 3 is used as a molecular probe.

Examples of the target compound 5 include a low molecular weight compound, a peptide, a protein, a glycoprotein, a virus, an extracellular vesicle and the like, and the target compound 5 can be an abused drug, an explosive, a poison, an agricultural chemical, an allergen, a mycotoxin, an odor component, a pathogen or a biomarker suggesting various diseases and health conditions such as cancer and the like. In particular, according to the method of embodiment, it is possible to obtain a high performance molecular probe for a low molecular weight compound, which has been difficult to obtain a corresponding molecular probe so far.

For example, the target compound 5 may be a substance contained in a liquid solvent. Examples of the liquid solvent include water, physiological saline, a buffer solution and the like, and the liquid solvent may optionally contain an organic solvent and a surfactant as necessary. The composition of the liquid containing the target compound 5 does not contain a substance that adversely affects determining of the molecular probe. Further, the liquid containing the target compound 5 may have the same composition as the solvent when the candidate molecule 3 is used as a molecular probe.

In the case where the target compound 5 is prepared as a liquid reagent, the solution 4 containing the candidate molecules 3 and the reagent are mixed in advance before step (S2) and the mixture may be added to the recess 2 of the first gel 1. Alternatively, the reagent may be added to the recess 2 or the entire first gel 1, before or after adding the candidate molecules 3 to the recess 2 of the first gel 1.

Alternatively, the target compound 5 may be a substance contained in a gaseous solvent. Examples of the gaseous solvent include air, nitrogen, oxygen, hydrogen, carbon dioxide and the like. The composition of the gas containing the target compound 5 has a does not contain a substance that adversely affects determining of the molecular probe. Further, the gas containing the target compound 5 may have the same composition as that of an environmental atmosphere in which the target compound 5 is to be detected.

In the case where the target compound 5 is prepared as a gaseous reagent, the reagent may be blown into the solution 4 containing the candidate molecules 3 in advance to obtain a mixture, and the mixture may be added to the recess 2 of the first gel 1. Alternatively, after the candidate molecules 3 is added to the recess 2 of the first gel 1, the gel may be placed in a container filled with the gaseous reagent or the like, and electrophoresis may be performed while exposing the candidate molecules 3 to the gaseous target compound 5.

Further, after adding the candidate molecules 3 to the recess 2 of the first gel 1, electrophoresis may also be carried out while the candidate molecules 3 is exposed to a volatile substance generated from the solid or liquid target compound 5, for example, by placing the gel in a container containing the solid or liquid target compound 5. In this case, even when some of the components of the target compound 5 are not volatile, it is possible to determine the candidate molecules 3 that bind to a volatile substance (i.e., an odorant and the like) unique to the target compound 5.

In the method of the embodiment, electrophoresis is performed by using the candidate molecules 3 of one kind, and it is used as an index that the candidate molecule is separated into a plurality of bands, or the band becomes broad in the electrophoresed direction. As necessary, the state of band can also be compared with the result of electrophoresis of the candidate molecules 3 not in contact with the target compound 5. Accordingly, the candidate molecule 3 bound to the target compound can be easily distinguished.

Further, according to the method for determining of the embodiment, there is no need to modify or immobilize the target compound. Accordingly, it is possible to select molecular probe(s) using the target compound 5 of the original structure. As a result, it is possible to determine the molecular probe of the target compound accurately. It is also possible to find molecular probe(s) that recognizes the whole structure of the target compound and binds to it, because the target compound 5 does not subject to modification or immobilization. Furthermore, the method of the embodiment is very easy to operate.

Second Embodiment

In the method according to the second embodiment, molecular probe(s) is determined by using a plurality of kinds of candidate molecules. FIG. 3 is an outline flow showing a method for determining a molecular probe according to the second embodiment. The method comprises the following steps:

(S11) electrophoresing a plurality of kinds of candidate molecules on a gel (a first electrophoresis);

(S12) making a target compound in contact with the candidate molecules on the gel after the first electrophoresis and electrophoresing an obtained mixture in a direction orthogonal to the direction of the first electrophoresis (a second electrophoresis); and (S13) determining the following candidate molecule(s) as the molecular probe that captures the target compound:

the candidate molecule(s) that is separated into a plurality of bands in the direction of the second electrophoresis, or the candidate molecule(s) that forms a broad band in the direction of the second electrophoresis on the gel after the second electrophoresis.

Figure 4:
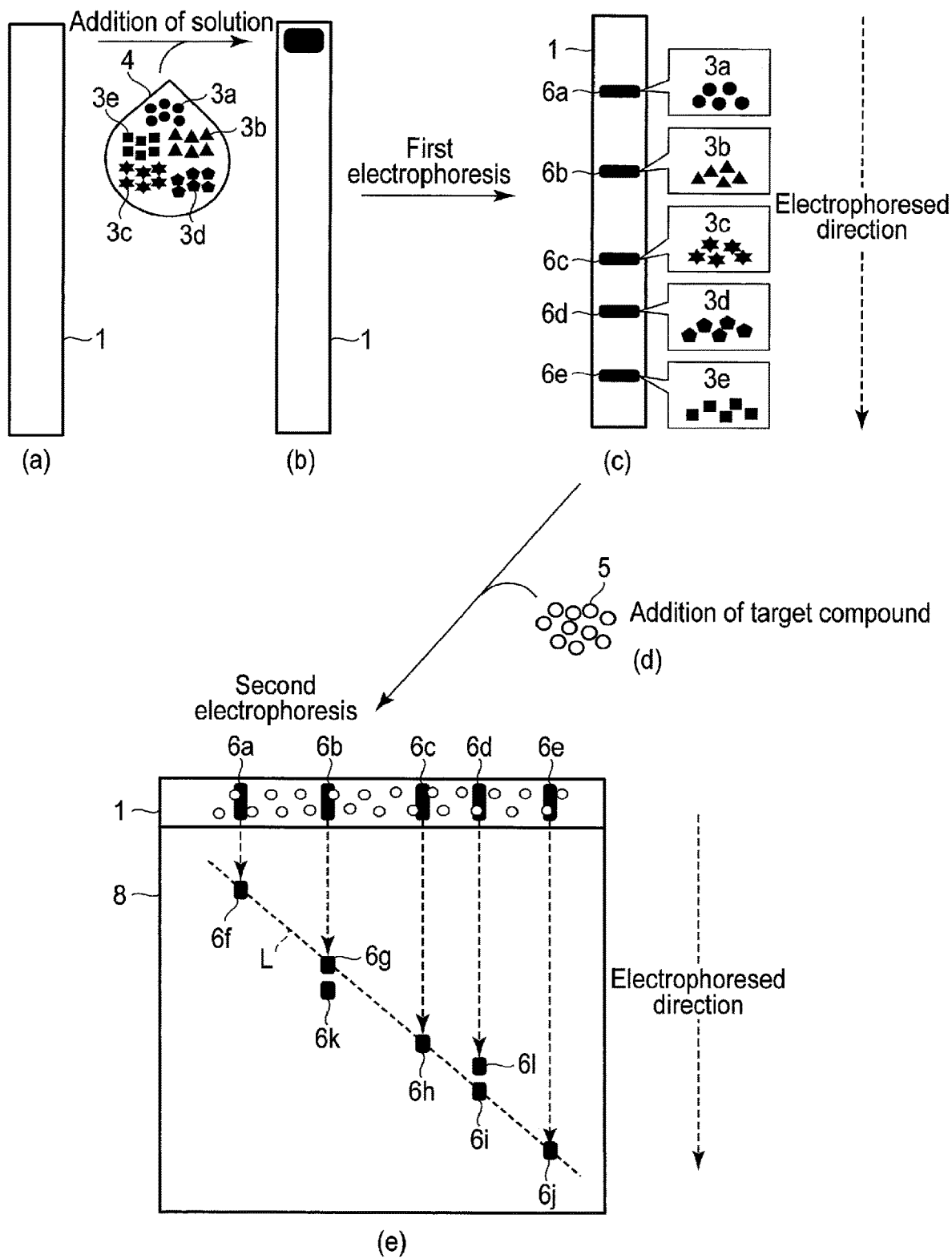
FIG. 4 shows schematic diagrams of the steps of a method for determining a molecular probe of one embodiment.

Hereinafter, the principle that a molecular probe capturing a target compound can be determined by performing each of the above steps is described with reference to FIG. 4. FIG. 4 is schematic diagrams showing the steps of the method of the second embodiment.

First, a solution 4 containing a plurality of kinds of candidate molecules 3 is prepared. The solution 4 contains five kinds of the candidate molecules 3a, 3b, 3c, 3d and 3e.

First, the solution 4 is added to a recess (not shown) formed at one end of a first gel 1 as shown in (a) and (b) of FIG. 4. Thereafter, electrophoresing is performed ((c) of FIG. 4). This electrophoresis is referred to as a first electrophoresis. The direction of the first electrophoresis is a direction from the end to which the solution 4 is added to the other end of the first gel 1.

As a result of the first electrophoresis, the candidate molecules 3a, 3b, 3c, 3d and 3e are separated depending on the differences in isoelectric point, molecular weight, higher order structure and the like according to the type of electrophoresis used. By this electrophoresis, the candidate molecules 3a, 3b, 3c, 3d and 3e are separated into bands 6a, 6b, 6c, 6d and 6e, respectively.

Next, as shown in (b) of FIG. 4, a target compound 5 is added to the first gel 1, and the target compound 5 is made into contact with the candidate molecules 3a, 3b, 3c, 3d and 3e ((d) of FIG. 4). And then, the side surface in the longitudinal direction of the first gel 1 is made to bind to the end of the second gel 8 ((e) of FIG. 4). Alternatively, after attaching the side surface in the longitudinal direction of the first gel 1 to the end of a second gel 8, the target compound 5 is added to the first gel 1 and the target compound 5 is made into contact with the candidate molecules 3*a*, 3*b*, 3*c*, 3*d*, and 3*e*. Alternatively, the target compound 5 is added to the second gel 8 in advance, and the side surface in the longitudinal direction of the first gel 1 is made to bind to the end of the second gel 8. For example, a liquid reagent containing the target compound 5 is added dropwise to the first gel 1 or the second gel 8. Alternatively, a gaseous reagent containing the target compound 5 is filled in a container, and the first gel 1 and the second gel are placed in the container. Alternatively, the first gel 1 and the second gel are placed in a container containing the solid or liquid target compound 5.

For example, as necessary, the gel may be allowed to stand for several minutes to several tens of minutes, so that the target compound 5 sufficiently comes in contact with the candidate molecules 3. Alternatively, the standing time may be determined according to the method of using the candidate molecules 3 as molecular probes. For example, when it is desired to detect a trace amount of the target compound with high sensitivity over time, it is preferable to increase the standing time enough. When it is desired to detect the target compound quickly, it is preferable to shorten the standing time.

Thereafter, electrophoresis is performed in a direction orthogonal to the direction of the first electrophoresis. This electrophoresis is referred to as a second electrophoresis. The direction of the second electrophoresis is a direction from the end of the second gel 8 to which the first gel 1 is bound to the other end of the second gel 8.

The second electrophoresis is performed using the same electrophoresis method as the first electrophoresis.

As a result of the second electrophoresis, the candidate molecules 3*a*, 3*b*, 3*c*, 3*d* and 3*e* move on the second gel 8 in the electrophoresed direction, respectively. The bands 6*a*, 6*c* and 6*e* each corresponding to the candidate molecules 3*a*, 3*c* and 3*e* which do not bind to the target compound 5 are not separated, but each of them is electrophoresed as one band (bands 6*f*, 6*h* and 6*j* in (e) of FIG. 4, respectively). In addition, the length of these bands 6*f*, 6*h* and 6*j* do not become broader in the first and the second electrophoresed directions beyond those assumed by free diffusion.

On the other hand, the bands 6*b* and 6*d* corresponding to the candidate molecules 3*b* and 3*d* that bind to the target compound 5 are separated into a plurality of bands in the second electrophoresed direction. Alternatively, the bands become broad in the second electrophoresed direction.

That is, the band 6*b* is separated into two bands: a band 6*g* corresponding to the candidate molecules 3*b* not bound to the target compound 5 and a band 6*k* corresponding to the candidate molecules 3*b* that binds to the target compound 5 and forms a complex. Alternatively, depending on the time for the candidate molecules 3*b* and the target compound 5 to have bound, a broad band is formed between the band 6*g* and the band 6*k*. The band 6*d* corresponding to the candidate molecules 3*d* is similarly separated into a plurality of bands 6*i* and 6*l*, or forms a broad band between the bands 6*i* and 6*l*.

Since the first electrophoresis and the second electrophoresis are performed using the same electrophoresis method, the electrophoretic distances of the candidate molecules 3*a*, 3*b*, 3*c*, 3*d* and 3*e* in the first electrophoresis and the electrophoretic distances of the candidate molecules 3*a*, 3*b*, 3*c*, 3*d* and 3*e* that are not bound to the target compound 5 in the second electrophoresis are the same. Accordingly, after the second electrophoresis, the bands 6*f*, 6*g*, 6*h*, 6*i* and 6*j* corresponding to the candidate molecules 3*a*, 3*b*, 3*c*, 3*d* and 3*e*, respectively that are not bound to the target compound 5 are lined up on the same straight line as shown in (e) of FIG. 4. Hereinafter, the one line connecting such bands 6*f*, 6*g*, 6*h*, 6*i* and 6*j* is referred to as "line L". The line L becomes a line descending toward the right when the direction of the first electrophoresis is the direction from the left side to the right side and the direction of the second electrophoresis is the direction from the upper side to the lower side in (e) of FIG. 4.

On the other hand, since the bands 6*k* and 6*l* are separated in the direction of the second electrophoresis, they are shifted from the line L. Depending on the type of the target compound and electrophoresis method used, the electrophoretic distance of the band corresponding to the complex may be longer than the band 6*g* as in the band 6*k* or may be shorter than the band 6*i* as in the band 6*l*.

From the above, the candidate molecules 3*b* and 3*d* separated into a plurality of bands in the direction of the second electrophoresis on the second gel 8 after the second electrophoresis can be determined as molecular probes that capture the target compound 5.

According to the method of the second embodiment, since two-dimensional electrophoresis is performed by the same electrophoresis method, bands of the candidate molecules not bound to the target compound 5 can be arranged on the line L. And the bands of the candidate molecules 3 bound to the target compound 5 are separated or become broad in the direction of the second electrophoresis, not in the longitudinal direction of the line L. Therefore, the bands of the candidate molecules 3 bound to the target compound 5 can be identified very clearly and easily. Accordingly, even when the target compound is a low molecular weight compound, it can be easily identified that a plurality of bands are formed, and the molecular probe can be determined. Further, according to such a method, since the target compound is not modified or immobilized, it is possible to determine an appropriate molecular probe accurately. Accordingly, even when the target compound is a low molecular weight compound, the molecular probe can be accurately determined.

The first electrophoresis and the second electrophoresis can be performed by any of the electrophoresis methods described in the first embodiment.

As the first gel 1, any of the gels described in the first embodiment selected according to the electrophoresis method used can be used. The second gel 8 is a gel having the same composition as that of the first gel 1. The first electrophoresis and the second electrophoresis may be performed consecutively using one gel having a size capable of performing two-dimensional electrophoresis.

As each candidate molecules 3, any one described in the first embodiment can be used. As with the first embodiment, each candidate molecule can be labeled such that it can be optically observed. Alternatively, as in the first embodiment, each candidate molecule can be labeled after performing electrophoresis.

One solution 4 can contain several kinds to over 1 million kinds of candidate molecules 3. For example, in the case where each candidate molecules 3 is a nucleic acid aptamer, in order to detect by fluorescent labeling, about 1 billion molecules is required for one kind. Even in the case of one million kinds of nucleic acid aptamer (candidate molecules), i.e., a total of $1.0^{15}$ nucleic acid aptamers, all of them can be subject to electrophoresis of the invention in one gel.

Alternatively, when the number of molecules per one kind is small, the line L can be detected, and therefore, it is possible to use to $1.0^{15}$ kinds of nucleic acid aptamers. This number corresponds to the number of all combinations of 25 base long nucleic acid sequences. However, in this case, since the number of molecules in the band that are away from the line L may be too small to be optically detected. In this case, the molecules are recovered blindly from the part of the gel other than the line L. The recovered molecules are then amplified by a method such as PCR, and electrophoresis is carried out again as necessary.

As a solvent of the solution 4, for example, the same solvent as in the first embodiment can be used. The composition of the solution 4 does not contain any substance that adversely affects each step of the method of the embodiment. Further, the solution 4 may have the same composition as the solvent when the candidate molecules 3 is used as a molecular probe.

As a reagent containing of the target compound 5, for example, the same reagent as in the first embodiment can be used. In the case where the reagent is a liquid, the liquid reagent may be made in contact with the candidate compounds by adding the reagent dropwise to the region containing the bands 6a, 6b, 6c, 6d and 6e on the first gel 1 after the first electrophoresis exist. When the reagent is a gas, the second electrophoresis may be performed by placing the combined first gel 1 and the second gel 8 in a container filled with the gaseous reagent. Alternatively, it is also possible to perform the second electrophoresis by placing the combined first gel 1 and the second gel 8 in a container containing the solid or liquid target compound 5.

Third Embodiment

The method according to the third embodiment is a method for determining a molecular probe(s) by using a plurality of kinds of candidate molecules. In this example, a target compound is made in contact with candidate molecules prior to the first electrophoresis.

Figure 5:
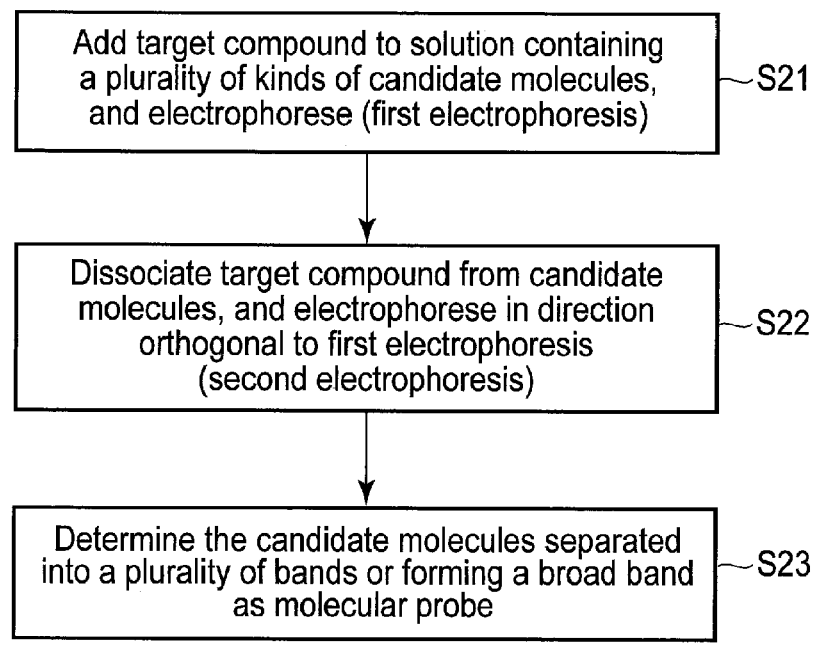
FIG. 5 shows a flowchart of a method for determining a molecular probe of one embodiment.

FIG. 5 is an outline flow showing a method for determining a molecular probe according to the third embodiment. The method comprises the following steps:
(S21) making a plurality of kinds of candidate molecules in contact with the target compound and electrophoresing an obtained mixture on a gel (a first electrophoresis);
(S22) making the target compound dissociate from the candidate molecules on the gel after the first electrophoresis, and electrophoresing the candidate molecules on the gel in a direction orthogonal to the direction of the first electrophoresis (a second electrophoresis); and
(S23) determining the following candidate molecule(s) as the molecular probe that captures the target compound:
the candidate molecule(s) that is separated into a plurality of bands in the direction of the first electrophoresis, or
the candidate molecule(s) that forms a broad band in the direction of the first electrophoresis on the gel after the second electrophoresis.

Figure 6:
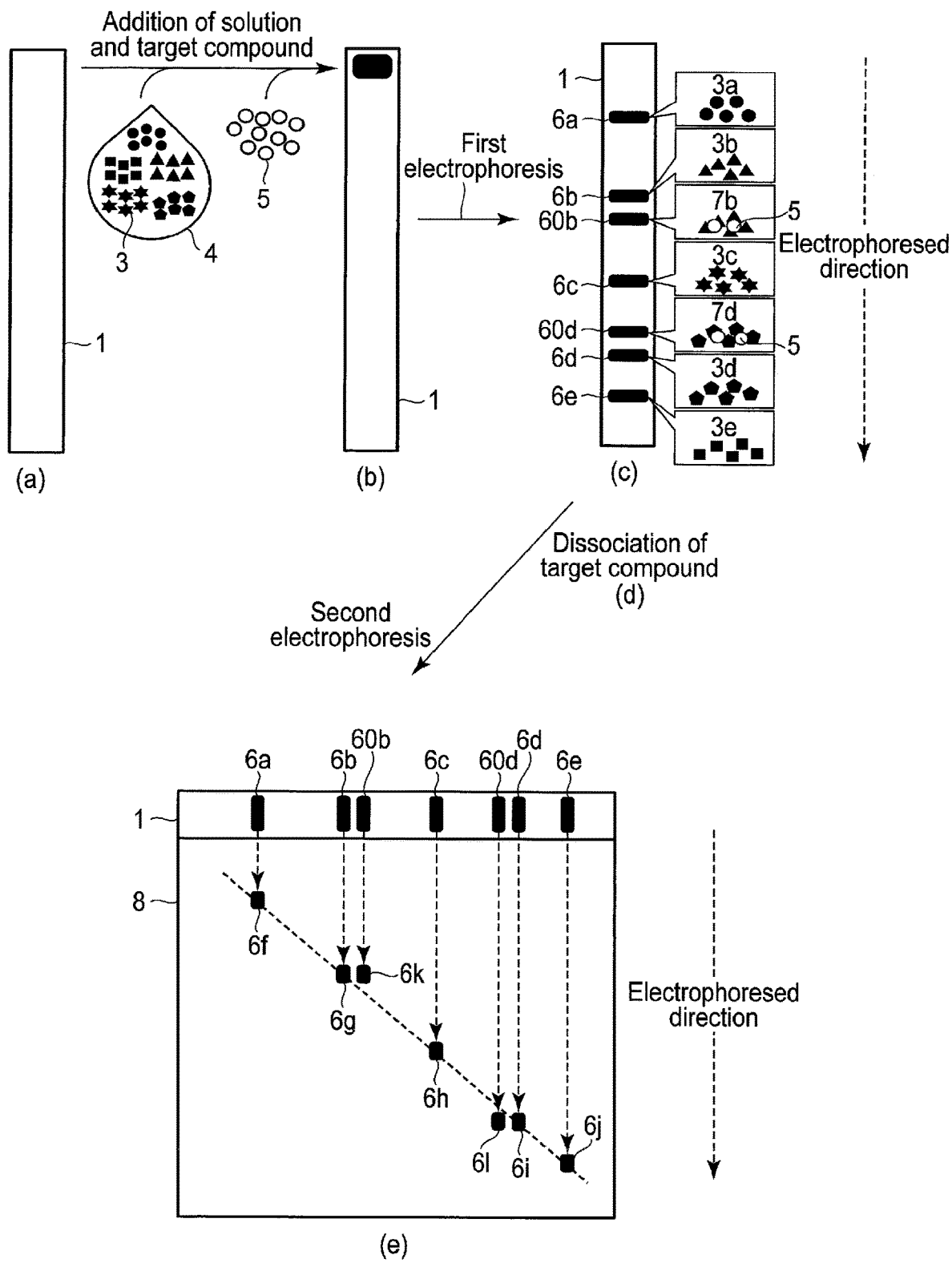
FIG. 6 shows schematic diagrams of the steps of a method for determining a molecular probe of one embodiment.

Hereinafter, the principle that the molecular probe capturing the target compound can be determined by performing each of the above steps is described with reference to FIG. 6. FIG. 6 is schematic diagrams showing the steps of the method of the third embodiment.

First, a solution 4 containing a plurality of kinds of candidate molecules 3 is prepared. For example, the solution 4 contains five kinds of the candidate molecules 3a, 3b, 3c, 3d and 3e.

First, the solution 4 and a target compound 5 are added to a recess (not shown) formed at one end of a first gel 1 shown in (a) and (b) of FIG. 6. As a result, the candidate molecules 3a, 3b, 3c, 3d and 3e are made in contact with the target compound 5. As a result of such a contact, some of the molecules of the candidate molecules 3b and 3d that bind to the target compound 5 may be bound to the target compound 5 to form complexes 7b and 7d, respectively. The other molecules of the candidate molecules 3b and 3d may remain unbound to the target compound 5. Alternatively, the molecules of the candidate molecules 3b and 3d transit between bound states 7b and 7d, and unbound states 3b and 3d respectively.

Thereafter, the mixture added to the recess is electrophoresed (a first electrophoresis) ((c) of FIG. 6). The direction of the first electrophoresis is a direction from the recess to which the solution 4 and the target compound are added to the other end of the first gel 1.

By the first electrophoresis, the candidate molecules 3a, 3b, 3c, 3d and 3e that are not bound to the target compound 5 are separated into bands 6a, 6b, 6c, 6d and 6e, respectively. In addition, the complexes 7b and 7d are separated into bands 60b and 60d, respectively. Alternatively, the bands become broad between the bands 60b and 6b and/or between the bands 60d and 6d according to the time during which the complexes 7b and 7d are formed. Depending on the target compound used and the type of electrophoresis method, the electrophoretic distances of the bands 60b and 60d may be longer than the band 6b as in the band 60b and may be shorter than the band 6d as in the band 60d.

Next, in the first gel 1, the target compound 5 is dissociated from the candidate molecules 3b and 3d ((d) of FIG. 6).

Next, as shown in (e) of FIG. 6, the side surface in the longitudinal direction of the first gel 1 is bound to the end of a second gel 8. Thereafter, electrophoresis is performed in a direction orthogonal to the direction of the first electrophoresis (a second electrophoresis). The second electrophoresis is performed using the same electrophoresis method as the first electrophoresis. The direction of the second electrophoresis is a direction from the end to which the first gel 1 is bound to the second gel 8 to the other end of the second gel 8.

As a result of the second electrophoresis, the bands 6a, 6b, 6c, 6d and 6e, and the bands 60b and 60d move in the electrophoresed direction, respectively.

Since the first electrophoresis and the second electrophoresis are performed using the same electrophoresis method, the electrophoretic distances of the candidate molecules 3a, 3b, 3c, 3d and 3e that are not bound to the target compound 5 in the first electrophoresis and the electrophoretic distances of the candidate molecules 3a, 3b, 3c, 3d and 3e that are not bound to the target compound 5 in the second electrophoresis are the same. Accordingly, bands 6f, 6g, 6h, 6i and 6j after the second electrophoresis of the bands 6a, 6b, 6c, 6d and 6e, respectively are lined up on the same straight rain as shown in (d) of FIG. 6.

On the other hand, as for the bands 60b and 60d, despite they are separated into positions different from the bands 6b and 6d in the first electrophoresis, but in the second electrophoresis, the electrophoretic distances of the bands 60b and 60d are the same as those of the bands 6g and 6i, because they are composed of the candidate molecules 3b and 3d not bound to the target compound 5. That is, the bands 60b and 60d are electrophoresed to the positions of bands 6k and 6l in (e) of FIG. 6.

Accordingly, after the second electrophoresis, each of the candidate molecules 3b and 3d is separated into a plurality of bands in the direction of the first electrophoresis. Alternatively, when the bands 60b and 60d are separated broadly between the bands 6b and 6d respectively, the bands after the second electrophoresis become broad between the bands 6g and 6k and between 6l and 6i. Accordingly, the candidate molecules 3b and 3d that are separated into a plurality of bands in the direction of the first electrophoresis or the candidate molecules 3b and 3d that form broad bands in the direction of the first electrophoresis can be determined as molecular probes that capture the target compound 5.

According to the method of the third embodiment, since two-dimensional electrophoresis is performed by the same electrophoresis method, bands of the candidate molecules not bound to the target compound 5 can be arranged on a line L. And the bands of the candidate molecules 3 bound to the target compound 5 are separated or become broad in the direction of the first electrophoresis, not in the longitudinal direction of the line L. Therefore, the bands of the candidate molecules 3 bound to the target compound 5 can be identified very clearly and easily. Accordingly, since the target compound is not modified or immobilized, it is possible to determine a molecular probe of a desired target compound accurately in an easy manner of operation.

In the case where the target compound 5 contained in a liquid reagent, the reagent and the solution 4 may be mixed in advance before step (S21) and the mixture may be added to the first gel 1. Alternatively, after the candidate molecules 3 are added to the first gel 1, the reagent may be further added thereto. In the case where the reagent is a gas, the gaseous reagent may be blown into the solution 4 and added to the gel, or the first gel 1 may be placed in a container filled with the gaseous reagent to perform the first electrophoresis.

Dissociation of the target compound 5 from the candidate molecules 3 in step (S22) can be performed, for example, by allowing the gel to stand for a desired time, or adding a reagent that causes dissociation of the bond with the target compound to the first gel 1, after the first electrophoresis, or the like.

Figure 7:
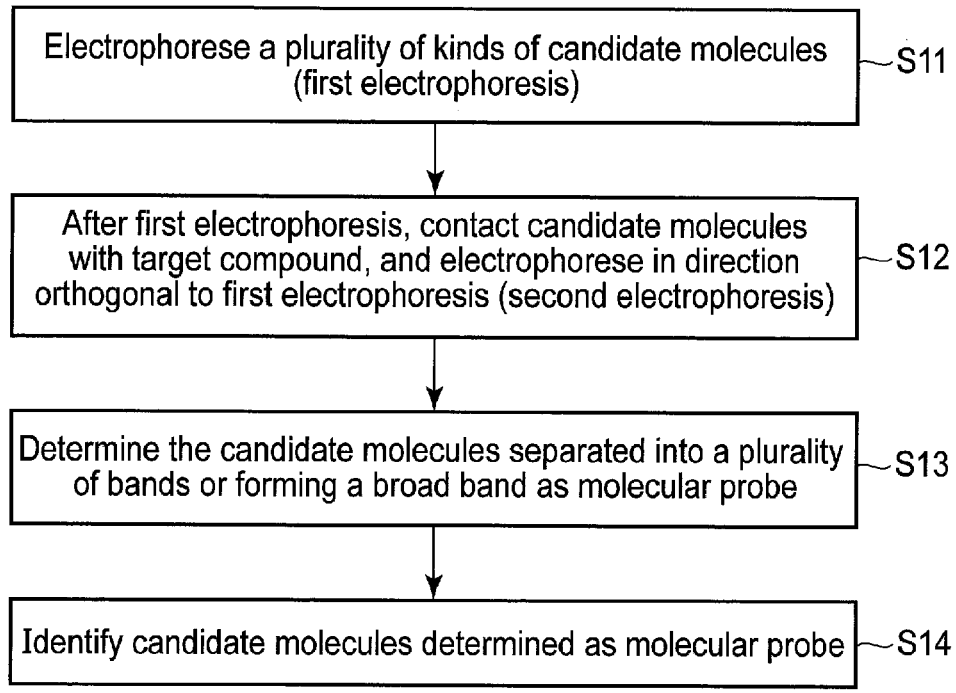
FIG. 7 shows a flowchart of a method for determining a molecular probe of one embodiment.
Figure 8:
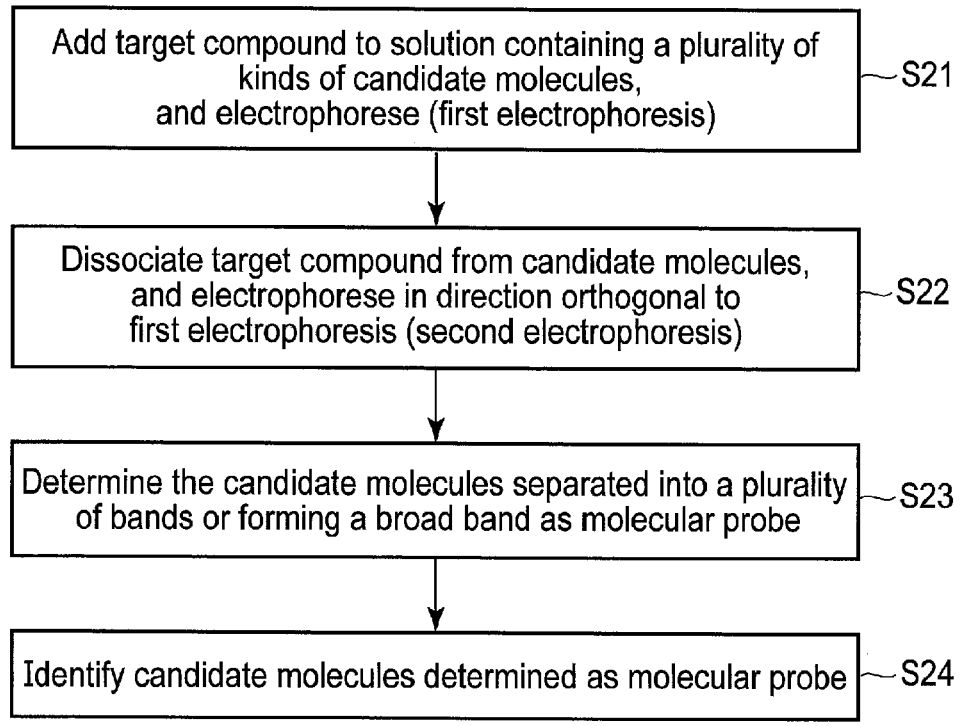
FIG. 8 shows a flowchart of a method for determining a molecular probe of one embodiment.

In a further embodiment, each of the methods according to the second embodiment and the third embodiment may further comprise step (S14) or (S24) that identifies a candidate molecule that is determined to be a molecular probe after step (S13) or (S23) of the method respectively. Outline flows of such methods for determining a molecular probe are shown in FIGS. 7 and 8.

For example, in the case of using a plurality of candidate molecules whose electrophoretic distances or the order of arrangement after being electrophoresed are known, candidate molecule(s) determined as molecular probe(s) may be identified from the electrophoretic distances or the order of arrangement of their bands after step (S13) or (S23). In the case of identification from the electrophoretic distance of the band, a standard reagent that forms band(s) serving as indicator(s) of the electrophoretic distance may be used in the second electrophoresis. The standard reagent may be electrophoresed together at a position that does not affect the band(s) of the candidate molecule(s) 3 on the second gel 8.

Alternatively, when the electrophoretic distance or the order of the arrangement of electrophoresed candidate molecule(s) is unknown, step (S14) or (S24) is performed, for example, as follows. First, a gel piece containing a band corresponding to a candidate molecule determined to be a molecular probe is excised from the gel after the second electrophoresis. Next, the candidate molecule is extracted from the gel piece and the candidate molecule is identified using any known analytical method selected according to the type of the candidate molecule.

For example, when the candidate molecule is a nucleic acid, the nucleic acid is extracted from the gel piece, and amplified, and sequenced. Alternatively, when the candidate molecule is a protein or a peptide, the candidate molecule is extracted from the gel piece and analyzed by known methods for identifying proteins or peptides. In the case where the candidate molecule is a protein or a peptide, the identification is more complicated than that of a nucleic acid, and therefore, it is preferable to adopt the method of the first embodiment that does not require identification of the candidate molecule.

As described above, when the candidate molecules 3 having binding ability to the target compound 5 comes into contact with the target compound 5, molecules of the candidate molecules 3 that do not bind to the target compound 5 exist with a very high probability. However, sometimes the observation of the band corresponding to the candidate molecules 3 that is not bound to the target compound 5 may be difficult, when most of candidate molecules 3 bind to the target compound 5. A method for determining a molecular probe in such a case is described with reference to FIG. 9.

Figure 9:
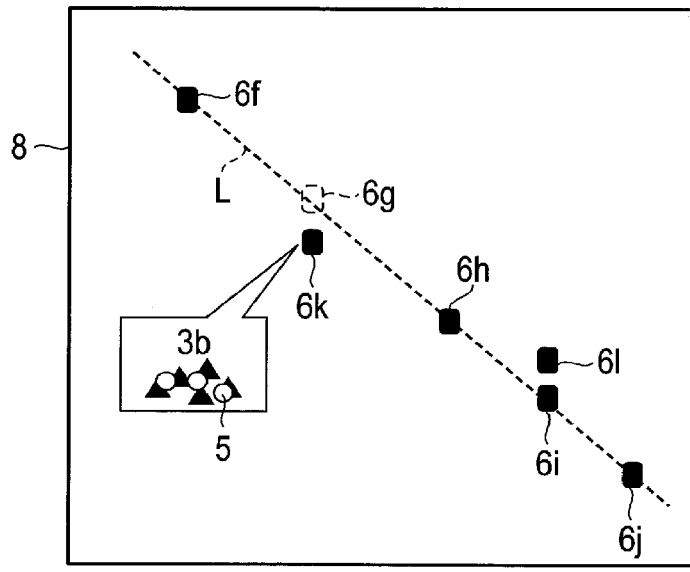
FIG. 9 shows schematic diagrams describing how to determine a molecular probe of one embodiment.
Figure 9:
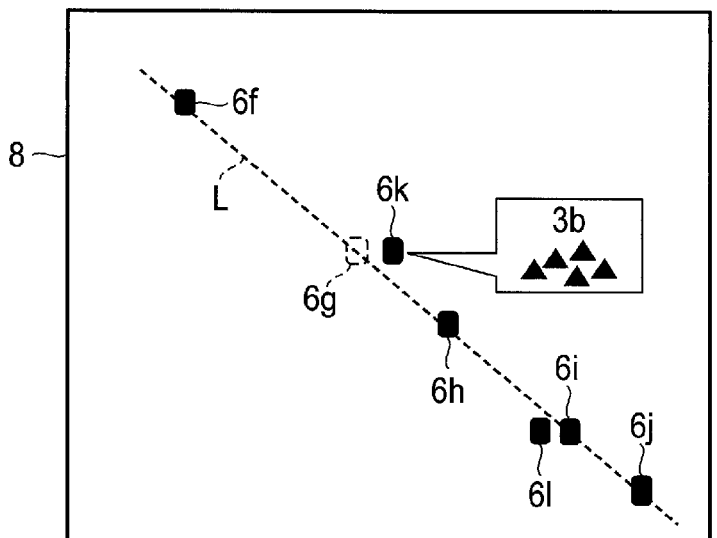

Part (a) of FIG. 9 shows the second gel 8 after the second electrophoresis in step (S12) in the second embodiment. In this example, it is shown that most of the candidate molecules 3b bind to the target compound 5, and it is difficult to observe the band 6g corresponding to the candidate molecules 3b. In this case, the band 6k corresponding to the candidate molecules 3b that is bound to the target compound 5 is shifted from the line L connecting the unseparated bands 6f, 6h and 6j in the direction of the second electrophoresis. In this manner, the candidate molecules 3 that form a band away from the line L can be determined as a molecular probe.

Part (b) of FIG. 9 shows the second gel 8 after the second electrophoresis in step (S22) in the third embodiment. In this example as well, it is possible to determine the candidate molecules 3 that produces a band shifted from the line L connecting the unseparated bands 6f, 6h and 6j into the direction of the first electrophoresis as the molecular probe.

For example, when there are two or more unseparated bands (for example, 6f, 6h or 6j), the line L can be determined as a line connecting these unseparated bands. Alternatively, a candidate molecule that binds to the target compound may produce a band at same electrophoretic distance as the candidate molecule that is not bound to the target compound. Such bands may be used to determine the line L.

In the case of using many kinds of candidate molecules in the methods of the second and the third embodiments, after the second electrophoresis, bands corresponding to the candidate molecules 3 that do not bind to the target compound 5, i.e., that are not separated, may be arranged without gaps, and may be observed itself as a line.

Figure 10:
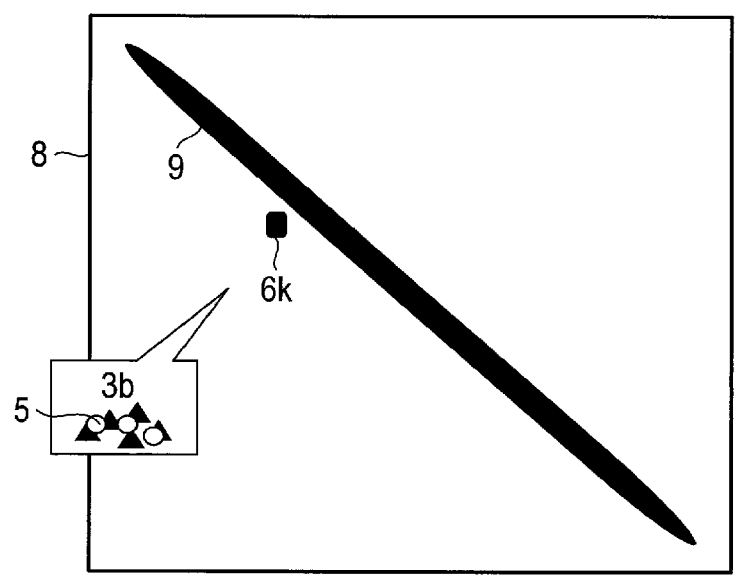
FIG. 10 shows a schematic diagram describing how to determine a molecular probe of one embodiment.

Such an example is shown in FIG. 10. In that case, the candidate molecules 3b contained in the band 6k observed at a position shifted from the observed line L on the second gel 8 can be determined as a molecular probe that captures the target compound. In the case of the second embodiment, the band 6k is shifted from the line L in the second electrophoresed direction, and in the case of the third embodiment, the band 6k is shifted from the line L in the first electrophoresed direction. Alternatively, in the same manner as the above-described embodiments, the band 6k may broaden as a line in the second electrophoresed direction in the case of the second embodiment and the band 6k may broaden as a line in the first electrophoresed direction in the case of the third embodiment, according to the distribution of the binding time between the candidate molecules 3b and the target compound 5. Accordingly, even when many candidate molecules 3 are used at a time, it is possible to distinguish the candidate molecules 3 that are bound to the target compound 5.

It should be noted that in the above-described examples, it is described that the molecular probe(s) is determined, but it does not necessarily mean that the molecular probe(s) is finally decided. For example, a plurality of candidate molecules can be extracted as potential candidates for molecular probes as a result of the above-described methods. In that case, other analysis methods and evaluation methods may be carried out after the above-described methods as necessary. Or the above-described methods may be carried out again, and then candidate molecules causing a larger change or clearer change may be selected. When the candidate molecule is a nucleic acid, the candidates of the molecular probe may be amplified by a technique such as PCR, and then determined again by the above-described methods.

Alternatively, many kinds of the candidate molecules may be narrowed down to a few kinds of the candidate molecules by the methods of the second or the third embodiment, and thereafter, may be finally determined by the methods of the first embodiment.

In addition, when the candidate molecule is a single-stranded nucleic acid, the 3-dimensional structure thereof may be unstable, and the band may be separated or may become broad even in a state where the target compound does not exist. Such a phenomenon is unpreferable because it may cause noise even when the candidate molecule is used as the molecular probe. Therefore, in this case, it is preferable that, for example, after finding conditions (for example, temperature, salt concentration, pH, and the like) where the separation or the broadening does not occur without the presence of the target compound, the molecular probe may be determined by the methods of the above-described embodiments. In addition, the conditions confirmed beforehand can also be used as conditions for detecting the target compound by using the candidate molecule as the molecular probe. Alternatively, the candidate molecule having unstable 3-dimensional structure may be deleted beforehand. For example, two-dimensional electrophoresis may be performed beforehand without target compound, only candidate molecules arranged on the line L may be collected, and then the electrophoresis of this embodiment may be carried out using collected candidate molecules.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A method for determining a molecular probe that captures a target compound, the method comprising:
   (i) electrophoresing a plurality of kinds of candidate molecules on a gel so as to obtain a plurality of bands of the candidate molecules on the gel (a first electrophoresis);
   (ii) making the target compound contact the plurality of bands obtained by the first electrophoresis so as to obtain a plurality of kinds of mixtures of the candidate molecules after the first electrophoresis and the target compound on the bands obtained by the first electrophoresis, and electrophoresing the plurality of kinds of mixtures in a direction orthogonal to a direction of the first electrophoresis (a second electrophoresis), the second electrophoresis obtaining a plurality of bands of the candidate molecules on the gel, into which at least one band of the plurality of bands obtained by the first electrophoresis is separated by the second electrophoresis in the direction of the second electrophoresis on the gel;
   (iii) determining the candidate molecules contained in the at least one band of the second electrophoresis as the molecular probe that captures the target compound; and
   (iv) extracting the candidate molecules determined as the molecular probe that captures the target compound,
   wherein an electrophoresis method used for the first electrophoresis and the second electrophoresis is the same.

2. The method of claim 1, wherein
   in the step (ii), the second electrophoresis further obtains at least one band of the candidate molecules on the gel that is not separated by the second electrophoresis, and
   the at least one band of the plurality of bands separated in the step (ii) is shifted in the direction of the second electrophoresis from a line connecting the at least one band of the candidate molecules that are not separated in the step (ii).

3. The method of claim 1, further comprising identifying the candidate molecule that is determined as the molecular probe.

4. The method of claim 1, wherein the target compound for the step (ii) is a substance contained in a gaseous solvent.

5. The method of claim 1, wherein the candidate molecules in the steps (i) to (iii) are labeled with a fluorescent dye, a dyestuff, or a radioisotope.

6. The method of claim 1, wherein the electrophoresis method used for the first electrophoresis and the second electrophoresis is an isoelectric focusing, or the first electrophoresis and the second electrophoresis are a native electrophoresis.

7. A method for determining a molecular probe that captures a target compound, the method comprising:
   (i) electrophoresing a plurality of kinds of candidate molecules on a gel so as to obtain a plurality of bands of the candidate molecules on the gel (a first electrophoresis);
   (ii) making the target compound contact the plurality of bands obtained by the first electrophoresis so as to obtain a plurality of kinds of mixtures of the candidate molecules after the first electrophoresis and the target compound on the bands obtained by the first electrophoresis, and electrophoresing the plurality of kinds of mixtures in a direction orthogonal to a direction of the first electrophoresis (a second electrophoresis), the second electrophoresis obtaining at least one band on the gel containing one of the candidate molecules, which is broader than at least one band of the plurality of bands obtained by the first electrophoresis in the direction of the second electrophoresis on the gel;
   (iii) determining the candidate molecules contained in the at least one band of the bands of the second electrophoresis as the molecular probe that captures the target compound; and (iv) extracting the candidate molecules determined as the molecular probe that captures the target compound, wherein an electrophoresis method used for the first electrophoresis and the second electrophoresis is the same.

8. The method of claim 7, further comprising identifying the candidate molecule that is determined as the molecular probe.

9. The method of claim 7, wherein the target compound for the step (ii) is a gas substance contained in a gaseous solvent.

10. The method of claim 7, wherein the candidate molecules in the steps (i) to (iii) are labeled with a fluorescent dye, a dyestuff, or a radioisotope.

11. The method of claim 7, wherein the electrophoresis method used for the first electrophoresis and the second electrophoresis is an isoelectric focusing, or the first electrophoresis and the second electrophoresis are a native electrophoresis.

12. A method for determining a molecular probe that captures a target compound, the method comprising:
(i) making a plurality of kinds of candidate molecules into contact with a target molecule and electrophoresing an obtained mixture on a gel so as to obtain a plurality of bands of the candidate molecules on the gel (a first electrophoresis);
(ii) making the target compound dissociate the plurality of bands obtained by the first electrophoresis so as to obtain a plurality of kinds of mixtures of the candidate molecules after the first electrophoresis and the target compound on the bands obtained by the first electrophoresis, and electrophoresing the plurality of kinds of mixtures in a direction orthogonal to the direction of the first electrophoresis (a second electrophoresis), the second electrophoresis obtaining a plurality of bands of the candidate molecules on the gel, into which at least one band of the plurality of bands obtained by the first electrophoresis is separated by the second electrophoresis in the direction of the first electrophoresis on the gel;
(iii) determining the candidate molecules contained in the at least one band of the second electrophoresis as the molecular probe that captures the target compound; and
(iv) extracting the candidate molecules determined as the molecular probe that captures the target compound,
wherein the first electrophoresis and the second electrophoresis are performed by the same electrophoresis method.

13. The method of claim 12, wherein
in the step (ii), the second electrophoresis further obtains at least one band of the candidate molecules on the gel that is not separated by the second electrophoresis, and
the at least one band of the plurality of bands separated in the step ii is shifted in the direction of the first electrophoresis from a line connecting bands the at least one band of the candidate molecules that are not separated in the step (ii).

14. The method of claim 12, further comprising identifying the candidate molecule that is determined as the molecular probe.

15. The method of claim 12, wherein the target compound for the step (ii) is a substance contained in a gaseous solvent.

16. The method of claim 12, wherein the candidate is molecules in the steps (i) to (iii) are labeled with a fluorescent dye, a dyestuff, or a radioisotope.

17. The method of claim 12, wherein the electrophoresis method used for the first electrophoresis and the second electrophoresis is an isoelectric focusing, or the first electrophoresis and the second electrophoresis are a native electrophoresis.

18. A method for determining a molecular probe that captures a target compound,
the method comprising:
(i) making a plurality of kinds of candidate molecules into contact with a target molecule and electrophoresing an obtained mixture on a gel so as to obtain a plurality of bands of the candidate molecules on the gel (a first electrophoresis);
(ii) making the target compound dissociate the plurality of bands obtained by the first electrophoresis so as to obtain a plurality of kinds of mixtures of the candidate molecules after the first electrophoresis and the target compound on the bands obtained by the first electrophoresis, and electrophoresing the plurality of kinds of mixtures in a direction orthogonal to the direction of the first electrophoresis (a second electrophoresis), the second electrophoresis obtaining at least one band on the gel containing one of the candidate molecules, which is broader than at least one band of the plurality of bands obtained by the first electrophoresis in the direction of the first electrophoresis on the gel;
(iii) determining the candidate molecules contained in the at least one band of the second electrophoresis as the molecular probe that captures the target compound; and
(iv) extracting the candidate molecules determined as the probe that captures the target compound,
wherein the first electrophoresis and the second electrophoresis are performed by the same electrophoresis method.

19. The method of claim 18, further comprising identifying the candidate molecule that is determined as the molecular probe.

20. The method of claim 18, wherein the target compound for the step (ii) is a gas substance contained in a gaseous solvent.

21. The method of claim 18, wherein the candidate molecules in the steps (i) to (iii) are labeled with a fluorescent dye, a dyestuff, or a radioisotope.

22. The method of claim 18, wherein the electrophoresis method used for the first electrophoresis and the second electrophoresis is an isoelectric focusing, or the first electrophoresis and the second electrophoresis are a native electrophoresis.

* * * * *